(12) United States Patent
Saunders

(10) Patent No.: US 6,682,903 B2
(45) Date of Patent: Jan. 27, 2004

(54) LIGAND BASED SOLUTION ASSAY FOR LOW CONCENTRATION ANALYTES

(76) Inventor: Alex M. Saunders, 8 Trillium La., San Carlos, CA (US) 94070

(*) Notice: Subject to any disclaimer, the term of this patent is extended or adjusted under 35 U.S.C. 154(b) by 104 days.

(21) Appl. No.: 09/976,235

(22) Filed: Oct. 12, 2001

(65) Prior Publication Data

US 2002/0123085 A1 Sep. 5, 2002

Related U.S. Application Data

(60) Provisional application No. 60/240,442, filed on Oct. 14, 2000, and provisional application No. 60/244,065, filed on Oct. 28, 2000.

(51) Int. Cl.$^7$ .............................................. G01N 33/53
(52) U.S. Cl. ...................... 435/7.92; 435/7.91; 435/18; 435/21; 436/164
(58) Field of Search ............... 435/7.91, 7.92, 435/18.21, 964, 188; 436/164

(56) References Cited

U.S. PATENT DOCUMENTS

| | | | |
|---|---|---|---|
| 3,975,237 A | | 8/1976 | Rubenstein et al. |
| 4,361,421 A | | 11/1982 | Bugaut et al. |
| 4,474,878 A | * | 10/1984 | Halbert et al. ............... 435/7.1 |
| 4,681,841 A | | 7/1987 | Matsumoto et al. |
| 4,687,735 A | * | 8/1987 | DiNello et al. .............. 435/7.1 |
| 4,810,631 A | | 3/1989 | Perlman et al. |
| 4,835,099 A | | 5/1989 | Mize et al. |
| 4,904,583 A | | 2/1990 | Mapes et al. |
| 5,100,436 A | | 3/1992 | Wenke |
| 5,183,941 A | | 2/1993 | Pan et al. |
| 5,306,621 A | | 4/1994 | Kricka |
| 5,583,001 A | | 12/1996 | Bobrow et al. |
| 5,843,666 A | | 12/1998 | Akhavan-Tafti et al. |
| 5,962,251 A | | 10/1999 | Rambach |
| 6,013,428 A | | 1/2000 | Langen et al. |
| 6,221,238 B1 | | 4/2001 | Grundig et al. |

FOREIGN PATENT DOCUMENTS

| | | |
|---|---|---|
| EP | 0 924 522 A2 | 6/1999 |
| WO | WO 95/04157 A1 | 2/1995 |
| WO | WO 98/21586 A1 | 5/1998 |
| WO | WO 98//21586 | 5/1998 |
| WO | WO 98/22822 A1 | 5/1998 |
| WO | WO 99/51767 A1 | 10/1999 |
| WO | WO 01/25476 A1 | 4/2001 |

OTHER PUBLICATIONS

Stefan Eichmüller, Paul A. Stevenson and Ralf Paus (1996) "A method for double immunolabelling with primry antibodies from identical species" *Journal of Immunological Methods* (255–265).
Bent, R. L. et al. (Jul. 1951). "Chemical constitution, electrochemical, photographic and allergenic properties of ρ–amino–N–dialkylanilines," *J. Am. Chem. Soc.* 73:3100–3124.
Gibbons, I. et al. (1987). "Nonseparation enzyme channeling immunometric assays," *Methods Enzymol.* 136:93–103.
Kricka, L. J. (1994). "Selected strategies for improving sensitivity and reliability of immunoassays," *Clin. Chem.* 40(3):347–357.
Kricka, L. J. and Ji, X. (1994), "Enhancement of peroxidase–catalyzed chemiluminescent oxidation of cyclic diacyl hydrazides by arylboronic acids," *Clin. Chem.* 40(9):1828–1830.
Litman, D. J. et al. (1983). "An internally referenced test strip immunoassay for morphine," *Clin. Chem.* 29(9):1598–1603.
Ornstein, L. (1959). "Localization of esterases and phosphatases with an indoaniline coupling system," *Histochem. & Cytochem.* 7:321.
Ornstein, L. and Ansley, H. R. (1974). "Spectral matching of classical cytochemistry to automated cytology," *Histochem. & Cytochem.* 22(7):453–456, 459–460, 463–465, 467–469.
Thornberry, N. A. and Lazebnik, Y. (Aug. 1998), "Caspases: enemies within," *Science* 281:1312–1316 (Review).
Valnes, K. and Brandtzaeg, P. (1984). "Paired indirect immunoenzyme staining with primary antibodies from the same species. Application of horseradish peroxidase and alkaline phosphatase as sequential labels," *Histochem. J.* 16:477–487.

* cited by examiner

Primary Examiner—Long V. Le
Assistant Examiner—Gary W. Counts
(74) Attorney, Agent, or Firm—Morrison & Foerster LLP

(57) ABSTRACT

The present invention provides an assay for an analyte in solution. The assay relies, in part, on associating two catalytic activities in close proximity to each other (e.g., by conjugating each enzyme to a ligand that binds the analyte) and providing substrates that produce a colored product only when both activities are bound to the same molecule in solution.

22 Claims, 5 Drawing Sheets

LIGAND BASED SOLUTION ASSAY FOR
LOW CONCENTRATION ANALYTES

CROSS-REFERENCE TO RELATED APPLICATIONS

This application claims benefit of U.S. provisional patent applications No. 60/240,442, filed Oct. 14, 2000, and No. 60/244,065, filed Oct. 28, 2000. The contents of each are incorporated herein.

FIELD OF THE INVENTION

This invention relates to calorimetric detection of analytes in a liquid sample, and finds application in the fields of biology, medical analysis, and analytical chemistry.

BACKGROUND

This section discusses a variety of methods for detection of compounds by the appearance of color. However, the citation of a reference or concept in this section should not be construed as an indication that the reference or concept is prior art to the present invention.

Detecting and measuring color is a convenient method for measuring the amount of a substance in solution. If the substance to be detected, i.e., the "analyte", does not have an inherent color, a color may be produced, as surrogate for the substance, by a variety of chemical, enzymatic or immunochemical methods. This well known art is practiced, for example, in both research and clinical laboratories of biological and health care fields. The principle of colorimetry is the constant loss of light in passage through a solution by absorbance of light into the colored compound. A molecular species absorbs the same amount of light in proportion to its concentration at the same wavelength every time it is measured. Light lost as it passes through a solution is determined by the concentration of the absorbing molecules and the length of the light path. By knowing the length of the light path and the light loss and the volume of the solution, it is possible to calculate the amount, or mass, of a substance. In practice, the calculation is frequently replaced by a standard curve represented by the same reaction on a series of known amounts of the same substance that have been processed by the same reactions to produce color. In alternative methods, the amount of light lost by scattering can be determined.

Ligand Assay

The sensitivity of a colorimetric test is defined as the limit amount that may be detected reliably using the method. One way to increase sensitivity (i.e., lower the limit amount to be detected), is to use an amplifier method for producing color. Amplifiers of special interest to life science assay design are catalysts, and especially the class of biological catalysts known as enzymes. Color reactions for the detection of enzymes or for the detection of the substrates on which enzymes operate as catalysts are well known. Sensitivity may be improved further by attaching enzymes to molecules that recognize the analyte, usually referred to as ligands.

ELISA

One standard assay for detecting and quantifying an analyte in a solution is the Enzyme Linked Immunosorbent Assay, or ELISA. However, this assay can be difficult to carry out and expensive. In this assay, after the enzyme linked ligand is joined to all analyte present in the assay, the excess enzyme linked ligand that is not attached to analyte must be eliminated from the solution or it produces unwanted amplification signal. The standard assay design includes a series of steps as follows:

One example of a standard container for such assays is a 96 well plate, so called because it has a matrix of 12 by 8 wells of standard size in a standard size frame. Manufacturers may treat such plates so as to permit strong attachment of certain molecular species to the well walls.

Adding a solution containing ligand to each well on the plate at 4° C. permits attachment and retains activity of ligand. This is an "overnight" procedure.

Plates are then washed to eliminate any ligand not firmly attached to the well wall. There are three sequential washes.

Plates are most often used immediately because the ligands so attached are not stable to storage. Sample or standard analyte solutions or blanks containing reagent only are added to individual wells. The analyte species, which forms the ligand pair, attaches to the ligand on the well wall.

After some period of incubation the plates are again washed to eliminate the remaining sample solution. There are three sequential washes Enzyme-conjugated ligand is then added to each well. Usually this ligand has specificity for another recognition site on the analyte molecule.

The plate is again washed to eliminate excess enzyme-conjugated ligand remaining in solution. There are three sequential washes. At this point the amount of enzyme attached to the wall of each well is determined by the amount of analyte also attached to the well wall.

Reagents are then added to test for the presence of the enzyme, and the color so produced relates to the amount of analyte added to each well.

Measurement is made in a photometer designed for reading the plates, called a plate reader.

It is apparent that ELISA is a tedious, time-consuming assay with many necessary steps. A manufacturer may perform the initial preparation of plates. Such manufactured plates are expensive. For example, one assay plate for performing 96 tests, may cost $650. In use, the assay using such a plate still takes approximately 5 hours to complete.

Channeling

One improvement over ELISA methods is known as "channeling" described in Gibbons et al., *Methods of Enzymology* 136:93. The principle of channeling is to form small, specialized particulates during the assay. The particulates permit attachment of ligands with two separate enzymes. The enzymes act in coordination, such that the product of one enzyme acts as substrate for the next. Only enzymes attached to the particles permit channeling. Enzyme not attached to particles do not produce color reaction product. Although this is a theoretical improvement over ELISA, there are considerations in formation of such specialized particles, which make this design impractical.

Other Solution Assays

Other solution assays using amplifiers are known. For example, U.S. Pat. No. 3,975,237 discloses a solution assay typically for small molecules. The assay principle is an inhibition of enzyme activity by use of a large molecule receptor, for example an antibody to the small molecular weight analyte, as competition to a small molecular version of the same analyte molecule. Methods of preparing conjugates of enzymes with analytes, and the sensitivity of assays of this nature are described. Another solution assay is described by Kricka and Ji, 1994, *Clinical Chemistry* 40:1828–30. This assay uses small molecule aryl boronic acids to enhance enzymatic luminescence. In a similar assay described in U.S. Pat. Nos. 5,843,666 and 5,306,621, the chemiluminescence is further enhanced by small molecule phenols. The method uses a binding partner labeled with a hydrolytic enzyme to produce a phenolic enhancer in close proximity to a peroxidase labeled specific binding partner. The mechanism of the enhancement is not known. This is a luminescence assay that uses expensive equipment that is not available to large numbers of laboratories, and has limited sensitivity.

Histochemistry

In the fields of histochemistry and cytochemistry, color contrast in tissues or cells is produced for purpose of microscopic examination or detection. Ligands that recognize tissue components and conjugated to enzymes are used as amplifiers that may then produce color with appropriate reagents. For visual examination it is possible to provide several colors of reaction product for several individual analytes with several different enzyme-conjugated ligands. This method is acceptable as long as the different analytes are located in different cells or tissue components. However, if the two analytes are present in the same location the resulting colors are additive, producing a new color which cannot be interpreted by microscopy. Another way to resolve two colors in one location is to use fluorescent markers. However fluorescence microscopy is much more expensive, and the automatic detection of fluorescence requires longer integration times, thus making automation of two color image detection impractical.

Color Photographic Development

Exposure of color film to light produces activated silver granules in the film. Light of different colors activates silver particles in different layers of the color film. During development with a common reagent, silver grains are reduced and thereby oxidize the common developer. The oxidized developer is captured in the layer chemically combines with color couplers. It is only the product of coupling oxidized developer and color coupler that produces color. Each layer has at least one coupler producing a color reaction product specific for that layer. Scavenger molecules, sometimes called "white couplers," prevent diffusion of developer from one layer to another. It is considered an advantage of the reaction of scavengers and colored couplers with oxidized developers if the reaction product is retained in the layer where it is formed. This is accomplished by designing or selecting couplers that are insoluble in the developer solvent both before and after coupling takes place. Some scavengers and some color couplers are designed with attachment to immobilized polymers. There are active regions on color coupler molecules and white couplers which enhance coupling to oxidized or activated photographic developers.

The chemical structure of the color couplers is highly similar to the reaction product of histochemical color producing compounds. Indeed the histochemical and cytochemical substrates are often the same as photographic color couplers with addition of a protective group on the active site. The protective group is hydrolyzed from the active region by action of the enzyme of interest. The chemical structure of photographic color developers is also very similar to substrates used in histochemistry of peroxidase reactions. The oxidized reaction product is also similar in histochemistry and in color photographic developers. In both chemical reactions the oxidation potential is also approximately the same. Use of photographic developers in detection of reaction products of hydrolytic enzymes was suggested by, for example Ornstein, 1959, *Histochemistry and Cytochemistry,* 7: 231 and Ornstein, 1974, *Histochemistry and Cytochemistry* 22:453–69, both incorporated by reference herein.

In the photographic industry it is well known that certain couplers form color more efficiently than others. By this is meant that they require less or more oxidized developer to form color. Since the amount of oxidized developer is determined by the number of sensitized silver ions, the effect is to require more sensitized silver ions for some couplers than for others. The more efficient couplers are known as 2-equivalent couplers, while the less efficient couplers are known as 4-equivalent couplers.

BRIEF SUMMARY OF THE INVENTION

The present invention provides an assay for analytes in solution. The assay relies, in part, on associating two catalytic activities in close proximity to each other to produce a detectable product. The invention takes advantage of the proximity of two catalytic activities, for example enzyme activities, to limit production of color, while the same enzymes not in proximity produce only minor background color. The present invention makes use of compounds analogous to protected color couplers and analogs to photographic color developers to produce color that is limited to regions in the solution where an oxidizing enzyme and a hydrolytic enzyme are in proximal location. In one embodiment of the invention white couplers are used as scavengers to inhibit color production in the solution where the enzymes are not in proximity.

The present invention has advantages over existing methods for detecting analytes in solution, such as ELISA. For example, the present assay can be carried out in multi-well (e.g., 96-well) plates without any wash steps to remove non-bound ligand, non-analyte molecules in the sample, and non-bound enzyme conjugated ligand. Without any attachment of capture reagent, analyte or detection reagent to the well wall, the present invention permits completion of a test within 1 to 1.5 hours. The results can be read using colorimetry plate readers, widely available clinical and research laboratories. Thus, the assay of the present invention is more rapid, has fewer steps, and is more economical than existing methods.

In one aspect, the invention provides a method for detecting an analyte in solution comprising (a) combining (i) a solution to be assayed for the presence or amount of the analyte; (ii) a first ligand capable of binding the analyte, wherein said first ligand is directly or indirectly bound to a first enzyme capable of cleaving a first substrate to produce a colorless first product, wherein said first enzyme is a hydrolase; (iii) a second ligand that binds the analyte, wherein the binding of the first ligand to the analyte does not interfere with the binding of the second ligand, and wherein the second ligand is directly or indirectly bound to a second enzyme capable of oxidizing a second substrate to produce a colorless second product, wherein said second enzyme is an oxidase; (iv) said first substrate; and, (v) said second substrate; whereby the hydrolase cleaves the first substrate to product the first product and the oxidase oxidizes that second substrate to produce the second product, wherein the first product and the second product chemically combine to produce a detectable reaction product, said detectable reaction product being a colored reaction product; (b) detecting the production of the colored reaction product; (c) relating the production of the colored reaction product with the presence of analyte in the solution. The method can further comprise combining a compound that is a scavenger for the first reaction product or the second reaction product in step (a). The scavenger can be 3-amino-1-(2,4,6-trichlorophenyl)-2-pyrazolin-5-one or acetoacetamide. The first substrate can be a compound that comprises a benzene ring or naphthalene structure with one active hydroxyl group, e.g., 1-naphthol phosphate or phenyl phosphate. The second substrate can be N,N-dimethyl paraphenylene diamine; N,N-diethyl paraphenylene diamine; N-phenyl paraphenylene diamine; N'-ethyl-N'ethyl-(2-methylsulfonamidoethyl)-2-methyl-1,4-phenylene diamine; 4 amino antipyrene; or N,N-dimethylamino benzidine. In various embodiments, the first ligand is a first antibody that specifically binds the analyte and second ligand is a second antibody that specifically bind the analyte, the hydrolase is a phosphatase, an esterases, a galactosidase, a lipase, a glucuronidase, an amidase, a peptidase, or a sulphatase. In an embodiment, for example the hydrolase is alkaline phosphatase and the oxidase is horseradish peroxidase. In an embodiment, the first substrate is naphthyl phosphate or phenyl phosphate and the second substrate is N'-ethyl-N'ethyl-(2-methylsulfonamidoethyl)-2-methyl-1,4-phenylenediamine. In some embodiments, at least one of the first and second ligand is an antibody or a lectin.

In a related aspect, the invention provides a method for detecting an analyte in solution comprising (a) combining (i) a solution to be assayed for the presence or amount of the analyte, wherein said analyte has an oxidase activity capable of acting on a first substrate to produce a colorless first product; (ii) a ligand capable of binding the analyte, wherein said ligand is directly or indirectly bound to a first enzyme capable of cleaving a second substrate to produce a colorless second product, wherein said first enzyme is a hydrolase; (iii) said first substrate; and, (v) said second substrate; whereby the hydrolase cleaves the second substrate to product the second product and the oxidase oxidizes the first substrate to produce the first product, wherein the first product and the second product chemically combine to produce a detectable reaction product, said detectable reaction product being a colored reaction product; (b) detecting the production of the colored reaction product; (c) relating the production of the colored reaction product with the presence of analyte in the solution. In an embodiment, the analyte has a pseudoperoxidase activity. In an embodiment, the analyte is glycated hemoglobin. In an embodiment, the solution comprises non glycated hemoglobin and the glycated portion of hemoglobin to be compared to total hemoglobin. In various embodiments, the ligand is an organic boronic acid compound directly or indirectly conjugated to a hydrolase. Further, the hydrolase can be alkaline phosphatase; the method can include combining a compound that is a scavenger for the first reaction product in step (a); the first substrate is selected from the group N,N-dimethyl paraphenylene diamine; N,N-diethyl paraphenylene diamine; N-phenyl paraphenylene diamine; N'-ethyl-N'ethyl-(2-methylsulfonamidoethyl)-2-methyl-1,4-phenylene diamine; 4 amino antipyrene; and N,N-dimethylamino benzidine, the second substate is naphthyl phosphate or phenyl phosphate, and the scavanger is 3-amino-1-(2,4,6-trichlorophenyl)-2-pyrazolin-5-one or acetoacetamide.

In a related aspect, the invention provides a method for detecting an analyte in solution comprising (a) combining (i) a solution to be assayed for the presence or amount of the analyte, wherein said analyte has a hydrolase activity capable of acting on a first substrate to produce a colorless first product; (ii) a ligand capable of binding the analyte, wherein said ligand is directly or indirectly bound to a first enzyme capable of cleaving a second substrate to produce a colorless second product, wherein said first enzyme is a oxidase; (iii) said first substrate; and, (v) said second substrate; whereby the hydrolase cleaves the first substrate to produce the first product and the oxidase oxidizes the second substrate to produce the second product, wherein the first product and the second product chemically combine to produce a detectable reaction product, said detectable reaction product being a colored reaction product; (b) detecting the production of the colored reaction product; (c) relating the production of the colored reaction product with the presence of analyte in the solution.

Stated differently, in various aspects and embodiment, the invention provides (1) A quantitative or qualitative colorimetric solution assay for analytes comprising: providing an analyte in solution; providing a first ligand to the analyte; providing a second ligand to the analyte; providing a catalytic activity for the first ligand to the analyte; providing a different catalytic activity for the second ligand to the analyte; providing a reagent for the first catalytic activity devised to give a first colorless reaction product; providing a reagent for the second catalytic activity devised to give a second colorless reaction product; devising conditions where the further reaction of the first reaction product and the second reaction product produces a colored third reaction product only when the first ligand and the second ligand are attached to the same analyte molecule; detecting the third reaction product by the amount of color produced and relating the detected color to the analyte in solution. In various embodiments: a reagent acting as a scavenger for the first or second reaction product is provided; the catalyst attached to the first ligand is an enzyme, such as an oxidase (e.g., horseradish peroxidase); the catalyst attached to the second ligand is an hydrolase enzyme (e.g., alkaline phosphatase); the second ligand is attached to a different epitope or attachment than the first ligand; first catalyst is horseradish peroxidase, the second catalyst is alkaline phosphatase, the first reagent is an oxidizable developer and the second reagent is naphthyl phosphate or phenyl phosphate; the oxidisable developer is N'-ethyl-N'ethyl-(2-methylsulfonamidoethyl)-2-methyl-1,4-phenylenediamine; the reaction comprises scavenger (e.g., 3-amino-1-(2,4,6-trichlorophenyl)-2-pyrazolin-5-one or acetoacetamide).

In various embodiment, at least one ligand is an antibody; or at least one ligand is a lectin; or at least one of the ligands is a molecule with more general affinity properties (e.g., a boronic acid compound)

In one aspect, the invention provides: a quantitative or qualitative colorimetric solution assay for analytes comprising: providing an analyte with a first catalytic activity in solution; providing a ligand to the analyte; providing a second catalytic activity for the ligand to the analyte; providing a reagent for the first catalytic activity devised to give a first colorless reaction product; providing a reagent for the second catalytic activity devised to give a second colorless reaction product; devising conditions where the further reaction of the first reaction product and the second reaction product produces a colored third reaction product only when the ligand is attached to the analyte; detecting the third reaction product by the amount of color produced and relating the detected color to the analyte in solution.

In various embodiments, a scavenger for the first or second reaction product is included, the catalyst analyte is an enzyme or pseudoenzyme; the enzyme is an oxidase (e.g., peroxidase or pseudoperoxidase) the catalyst attached to the ligand is a hydrolase enzyme (e.g., alkaline phosphatase); the ligand is attached to a different epitope or attachment than the enzyme or active site of the analyte; the first catalyst is a peroxidase, the second catalyst is alkaline phosphatase, the first reagent is an oxidizable developer and the second reagent is naphthyl phosphate or phenyl phosphate.

In various embodiments, the first catalyst is glycated hemoglobin; there is present in the analyte sample a quantity of non glycated hemoglobin and the result to be determined is the determination of the glycated portion of hemoglobin compared to total hemoglobin; the oxidizable developer is N'-ethyl-N'ethyl-(2-methylsulfonamidoethyl)-2-methyl-1,4-phenylenediamine; a scavenger reagent is included (e.g., 3-amino-1-(2,4,6-trichlorophenyl)-2-pyrazolin-5-one or acetoacetamide); the ligand is an antibody; the ligand is a lectin; the ligand is a molecule with more general affinity properties (e.g. a boronic acid compound, attached to alkaline phosphatase.

In a related aspect, the invention provides a kit for solution assays comprising a first antibody to an analyte conjugated to a first enzyme with peroxidase activity, a second antibody to the same analyte conjugated to a second enzyme with alkaline phosphatase activity, a source of hydrogen peroxide, an oxidizable developer, a phenol like substrate for alkaline phosphatase and a colorless coupler to use as scavenger. In an embodiment, the oxidizable developer is N'-ethyl-N'ethyl-(2-methylsulfonamidoethyl)-2-methyl-1,4-phenylenediamine, the substrate is phenyl phosphate or naphthyl phosphate and the scavenger is acetoacetamide. The invention also provides a kit for detecting the proportion of glycated to total hemoglobin comprising a well plate suitable for measurement in a plate reader, an enzyme with alkaline phosphatase activity coupled with a boronic acid, a source of hydrogen peroxide, an oxidizable developer, a phenol like substrate for alkaline phosphatase and a colorless coupler to use as scavenger. In an embodiment, the oxidizable developer is N'-ethyl-N'ethyl-(2-methylsulfonamidoethyl)-2-methyl-1,4-phenylenediamine, the substrate is naphthyl phosphate and the scavenger is acetoacetamide.

DETAILED DESCRIPTION OF THE INVENTION

Overview

The present invention provides a method for detecting an analyte in solution. In one embodiment, a hydrolase enzyme activity and an oxidase enzyme activity are brought into close proximity by joining both enzymes to a single analyte molecule and appropriate substrates provided such that the hydrolase acts on one substrate to produce a non-colored soluble product, the oxidase acts on a second substrate to produce a non-colored soluble product, and, provided the two products are produced in close proximity, they chemically combine to produce a soluble colored product that can be detected. The appearance of the colored product is correlated with the quantity of the analyte in the sample, e.g., by using a standard curve. In a preferred embodiment, one or more scavenger(s) is present during the reaction that reacts with uncolored product(s). As used herein, the terms "chemically combine," refers to the formation of a covalent chemical linkage between two reaction products, resulting in a third product that is detectable and distinguishable from the two reaction products.

Figure 1:
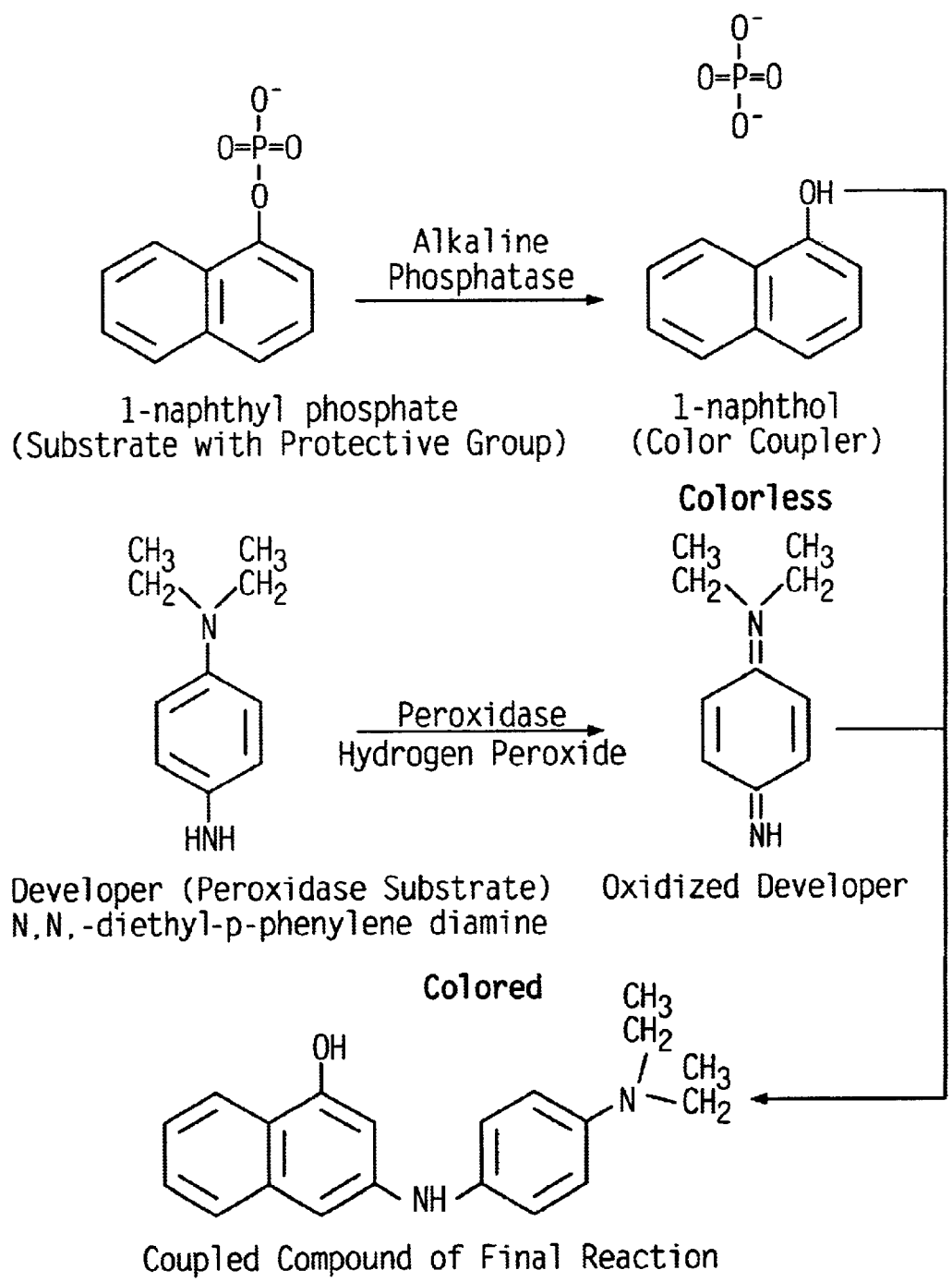
FIG. 1 provides an exemplary reaction of the type that can be used in the present invention.

A summary of one embodiment of the method is provided in FIG. 1, for illustration and not limitation. A variety of other embodiments are disclosed herein. In addition, a variety of histochemical and cytochemical principles and reagents are disclosed in U.S. patent application Ser. No. 09/411,352, published Apr. 12, 2001 as WO 01/25476, which can be applied in the present method, provided that combinations of the reagents are selected to remain soluble. This can be accomplished by selecting or modifying reagents to increase solubility, or, alternatively, by including a solubilizing agent (e.g., 1–10% ethanol, diethylene glycol, and the like) in the reaction mixture. In the present method, proximity of two enzymatic activities at the molecular level is required, which means that the two primary reaction products must react together to form a final reaction product in molecular proximity.

Analyte

As used herein, the term "analyte" refers to the compound in solution to be detected using the assay of the invention. The analyte can be any of a variety of compounds or macromolecular complexes in solution such as, without limitation, a polynucleotide, an antigen, a hapten, an antibody, a viral particle, and the like. In one embodiment, as described below, the analyte has an enzymatic activity. The term "solution," as used herein, refers to an aqous solution which can be a buffered solution, a homogenate (e.g., cell homogenate), a body fluid (e.g., plasma, urine, cerebrospinal fluid), an extract or partially purified compound, or the like, suspected of containing the target analyte. The methods of the present invention are most useful for detection of analytes at low concentration (e.g., typically less than 10 micrograms/ml, often less than 1 microgram/ml).

Ligands and Ligand Conjugates

The present invention employs binding molecules, also called "ligands," that bind an analyte molecule in solution. Typically the binding is non-covalent. In one embodiment of the invention, two ligands are used which bind to the same analyte molecule. For example, in one embodiment, two antibodies (ligands) bind two different epitopes of a protein or macromolecular complex. That is, the antibodies are paired antibodies to the same analyte, but with a different specific binding site (epitope) on the same analyte. When used in the context of ELISA tests, such antibody pairs are often referred to as a "capture antibody" and a "detection antibody."

Suitable antibodies for use in the invention include monoclonal antibodies, binding fragments (e.g. Fab fragments), single chain antibodies, and the like. In addition to antibodies, suitable ligands include lectins (which specifically bind carbohydrates) and other binding molecules described herein or well known in the art (e.g., biotin, avidin, protein A). An inhibitor analog of a substrate that binds to an enzyme active site is another example of a ligand. As used herein, no particular biological function, other than selective binding to the analyte, is implied by use of the term ligand. Certain small (i.e., molecular weight less than 1000) molecules have specificity for a class of structures and are useful in analysis. For example boronate-containing compounds have an affinity for hydroxyl groups on two or more adjacent carbon atoms. Boronate conjugated enzymes, for example aminophenyl boronic acid conjugated to alkaline phosphatase can be used as ligands for the detection of carbohydrates (e.g., provided the other component of the paired enzyme conjugate has sufficient specificity, as described below).

The ligand(s) is directly or indirectly bound, or coupled to, an enzyme or other catalyst. As used in this context, "direct" binding means that the catalyst (enzyme) is covalently bound to the ligand (e.g., antibody). Indirect binding refers to any of a variety of art-known means for covalently or non-covalently associating an enzyme with a binding molecule: examples include use of an enzyme labeled secondary antibody that binds a primary (anti-analyte) antibody, biotin-avidin mediated binding, and the like. Stated differently, ligands for conjugation with the enzymes include antibodies that are specific for the analytes to be measured. The well-known ligand pairs such as the avidin-biotin pair may be applied as secondary linkages to provide a more versatile reagent. For example a biotinylated nucleotide may be used in a hybridization assay where temperature of the procedure may inactivate a directly linked enzyme. Following hybridization the enzyme may be linked through avidin to the hybridized molecule.

Enzyme-ligand Conjugates

In certain embodiments in which two ligands are used, each of the two is conjugated to an enzyme (i.e., protein catalyst) with a different substrate specificity (i.e., a different enzyme). In one embodiment, one ligand is conjugated to an oxidase and a second ligand is conjugated to a hydrolase. It will be apparent that when the analyte of interest is one half of a ligand pair, and the other half is attached to an enzyme amplifier, then the analyte is indirectly also joined to the enzyme which is used as an amplifier.

Oxidase Enzymes

Oxidases are enzymes that catalyze the oxidation of a substrate. Any of a variety of oxidase enzymes are suitable for use in the invention. Usually, the oxidase can use a photographic developer as substrate. Photographic developers, as is well known, are soluble organic compounds characterized by susceptibility to oxidation by sensitized silver ions, but not by nonsensitized silver ions, and the ability to couple with a second compound having an active site. Virtually all photographic developers are N,N-alkyl substituted para phenylenediamines. Suitable oxidases include peroxidases (e.g., horseradish peroxidase, myeloperoxidase), galactose oxidases, cytochrome oxidases, monoamine oxidases, pseudoperoxidases, and others. In some embodiments, as described herein, the analyte itself may have an oxidase activity (i.e., an endogenous oxidase activity). Examples of such analytes with endogenous oxidase activity include the pseudoperoxidase activity of the hemoglobin and the myoglobin molecules.

Oxidase Substrates

Generally, any oxidase substrate which is converted by an oxidase (e.g., peroxidase) to a product capable of coupling with a color coupler (described herein below) to produce a soluble reaction product may be used in the methods disclosed herein. Suitable substrates include those with the same molecular structures as well-known photographic developers. Exemplary substrates (sometimes referred to as "developers," "photographic developers," or "color developers") include N,N-dimethyl paraphenylene diamine; N,N-diethyl paraphenylene diamine; N-phenyl paraphenylene diamine; N'-ethyl-N'ethyl-(2-methylsulfonamidoethyl)-2-methyl-1,4-phenylene diamine; 4 amino antipyrene; N,N-dimethylamino benzidine. A larger list of fifty such photographic developers may be found in Bent et al., 1951, *J. Am. Chem. Soc.* 73:3100–24, incorporated by reference herein in its entirety. Additional oxidases and substrates useful in the present invention are described in copending U.S. patent application Ser. No. 09/0411,352, published Apr. 12, 2001 as WO 01/25476, both incorporated by reference herein in its entirety for all purposes. Developer peroxidase substrates may have chemical groups added to the phenyl ring without detriment to their reaction, and some groups are helpful in design of certain assays. For example a methyl group ortho to the primary amine is known in the photographic industry to prevent autopolymerization of the oxidized developer. The dialkyl amine of N,N dialkyl substituted phenylene diamine may also be beneficially modified. For example, addition of a sulphonamido group augments solubility of the final reaction product.

Autopolymerization may be used as a design feature which is useful for some assays. For example, autopolymerization effectively prevents an oxidized developer molecule from coupling with a color coupler if the coupling is not accomplished immediately after the oxidation. The comparable speeds of coupling and autopolymerization, two competitive reactions, will determine the diffusion distance from original production at which color formation may occur. However, if the reaction is prolonged, there is a tendency for autopolymerized developer to precipitate and thereby change the optical characteristics of the solution to that of a suspension. Therefore a developer compound without a methyl group ortho to the primary amine is more useful in rapid reactions, while a compound with such a methyl group is used in design of an assay that develops slowly. The latter assay is also more likely to require a scavenger, as described below.

A preferred developer is N-ethyl-N-ethyl-(2-methylsulfonamidoethyl)-2-methyl-1,4-phenylenediamine. Thus, in one embodiment, N,N dialkyl substituted phenylenediamine is used as substrate in combination with a peroxidase.

It will be appreciated that, depending on the enzyme, certain cofactors may be required for the oxidation reaction. For example, when a peroxidase enzyme is used, hydrogen peroxide is also used as a cosubstrate for the oxidation reaction. When certain oxidases are used, cytochrome C may be required as a cofactor.

Hydrolase Enzymes

Hydrolases are enzymes that catalyze a hydrolysis reaction, e.g., capable of removing a protecting moiety from a substrate (color coupler) to produce a reactive product (color coupler). Exemplary hydrolases include phosphatases (e.g., alkaline phosphatase), esterases (e.g., cholinesterases, carboxyl esterase), galactosidases (e.g., alphanaphthol betagalactosidase), lipases, glucuronidases, amidase, peptidases, and sulphatases. These are all well known in the art (see, e.g., U.S. Pat. No. 3,975,237, incorporated herein by reference). Preferred hydrolytic enzymes are those which are more active at alkaline pH, because these are the conditions preferred by the photographic chemical compounds. A particularly preferred enzyme, for reasons of economy and commercial availability, is alkaline phosphatase.

Hydrolase Substrates

Substrates for hydrolases include esters, amides, peptides, ethers, or any chemical compound having an enzymatically hydrolyzable covalent bond. The enzyme catalyzed hydrolysis reaction results in a hydroxyl or an amine compound as one product (and free phosphate, acetate, etc., as a second product). Hydrolase enzyme substrated used in the present invention are those converted to a color coupler by the action of the enzyme by removal of a blocking group. The presence of the blocking group prevents the chemical combination of the substrate with the oxidized developer. Thus, typically the substrate has the formula: "R—B", where "R" is a color coupler moiety "—B" is a blocking group such as a phosphate, a sulfate, an acetate or a butyrate, or the like, linked to the color coupler moiety by an enzyme-cleavable (e.g., hydrolase-cleavable) linkage such as an ester (including a phosphate ester or a sulfate ester) linkage or an amide linkage.

The preferred substrate for the hydrolase is a substituted (protected) phenol or naphthol compound (e.g., a preferred substrate for alkaline phosphatase is a phosphate-substituted phenol or naphthol compound. The substrates generally preferred for histochemistry and cytochemistry applications are not preferred substrates for the present invention because they are designed to precipitate in the tissues or cells localizing the enzyme activity. The preferred substrates for the present invention are smaller molecules, such as 1-naphthol phosphate, or phenyl phosphate, which remain in solution after hydrolysis and also after coupling with the preferred developer. Substitutions on these simple naphthol and benzene compounds may enhance the reactivity or formation of the preferred color without detriment to their use. For example substituting a chlorine group in the position para to the phosphate group permits faster coupling and a more efficient reaction because chlorine acts as a leaving group in the position to which the oxidized developer couples. These more efficient substrates are comparable to 2-equivalent couplers known in the photographic industry. (In the photographic industry it is well known that certain couplers form color more efficiently than others, i.e., they require less or more oxidized developer to form color. Since the amount of oxidized developer is determined by the number of sensitized silver ions, the effect is to require more sensitized silver ions for some couplers than for others. The more efficient couplers are known as 2-equivalent couplers, while the less efficient couplers are known as 4-equivalent couplers.) The choice of a 2-equivalent or 4-equivalent coupler type of substrate is determined by the relative activity of the two enzymes in any specific assay described in this invention. For example, twice as much active peroxidase has to be in proximity of the hydrolase when using a 4-equivalent coupler than when using a 2-equivalent coupler. Avidin is a tetravalent ligand, and when using Avidin-conjugated hydrolase there will be multiple liganded oxidases in proximity and a 4-equivalent coupler is acceptable. When the enzymes in ligand related proximity are in 1:1 proportion, a 2-equivalent coupler is efficient.

Substrates for hydrolytic enzymes usually contain the enzyme specific component adjacent to the benzene or naphthalene ring. In various embodiments, the substrate comprises a substituted phenol or naphthol compound, i.e., a compound that comprises a benzene ring or naphthalene structure with one active hydroxyl group protected by the enzyme-specific substrate composition, and having at least one carbon in the ring in a position ortho or para to the active hydroxyl group where a substitution reaction may take place. Such ortho or para position may be covered by hydrogen or by a halogen or other group which readily leaves the ring structure during a substitution reaction. The substrate active component is a specific structure varying with each enzyme. The substrate for sulphatase may be 1-naphthyl sulfate. The substrate for each caspase is a four amino acid peptide, which varies with the specific caspase, but always has an aspartate residue adjacent to the naphthol or phenol. After action of enzyme on the substrate, the benzene or naphthalene will have a free (unprotected) hydroxyl group at the site where the specific substrate component was attached. The free hydroxyl activates the ortho, or preferentially, the para position on the ring and permits coupling in these positions. If a halogen, carboxyl, or other efficient leaving group, is substituted in the ortho or para position then coupling in that position replaces the leaving group during the coupling reaction and the reaction is more efficient than in an unsubstituted naphthalene or benzene ring. Conversely a nitro or other strongly binding substituent in the ortho or para positions on the phenol will prevent coupling in that position but may permit coupling in the alternate para or ortho position. For example, para-nitrophenyl phosphate, after cleaving the phosphate becomes para-nitrophenol which is not an efficient coupler with oxidized developers. The "leaving group" truly leaves during a coupling reaction, and the resulting color compound has the same color whether there was a leaving group present or not. For example 4-chloro-1-naphthol or 1-naphthol coupled to N,N-diethyl-para-phenylene diamine have identical light absorption spectra, but coupling (measured by development of color) of the 4-chloro is at least twice as fast.

The naphthol AS substrates which are preferable in histochemistry because their unprotected reaction products are poorly soluble in aqueous solutions are not preferred substrates for the solution assay. Just the opposite is preferred, in that a solubilizing group such as a sulphonic acid on the opposing ring to the hydroxyl group, for example 8-hydroxy-1-naphthalene sulphonic acid produces a highly colored, very soluble, coupled compound with a very sharp absorption peak in the far blue region of the spectrum. An equivalent 8-phospho-1-naphthalene sulphonic acid would not couple and there would be no color. The following table provides hydrolase substrates. In the table, exemplary hydrolases are provided along with blocking groups that can be conjugated to chromogenic moieties (i.e., color couplers). Part A shows the hydrolase and group recognized by the enzyme, which is linked by a hydrolysable bond ("—") to a chromogenic group such as those shown in Part B of the table.

TABLE 1

Hydrolase Substrates for Solution Assays
Substrate specific component is linked to the chromogenic coupler through
a covalent bond indicated by two dashes (--) in the following tables.

Part A: Hydrolases and Substrate specific components (Examples)

1. Caspases

| | |
|---|---|
| Caspase 1 | Ac—Tyr—Val—Ala—Asp-- |
| Caspase 3 | Ac—Asp—Glu—Val—Asp-- |
| Caspase 4 | Ac—Leu—Glu—Val—Asp-- |
| Caspase 5 | Ac—Trp—Glu—His—Asp-- |
| Caspase 6 | Ac—Val—Glu—Ile—Asp-- |
| Caspase 9 | Ac—Leu—Glu—His—Asp-- |

TABLE 1-continued

Hydrolase Substrates for Solution Assays
Substrate specific component is linked to the chromogenic coupler through
a covalent bond indicated by two dashes (--) in the following tables.

2. Glycosidases

| | |
|---|---|
| Glucosidases | Glucose-alpha- |
| (alpha and beta) | Glucose-beta- |
| Galactosidases | Galactose-alpha- |
| | Galactose-beta- |
| Glucosaminidase | N-Acetyl glucosamine-- |
| Glucuronidase | Glucuronic acid-- |

3. Peptidases and proteinases

| | |
|---|---|
| Collagenase 1 | HO—Darg—Gln—Gly—Ala—Ill—Gly—Gln—Pro-- |
| Elastase III | Pyr—Pro—Val-- (Pyr = pyroglutamyl) |
| Trypsin | Benzoyl DL Arginine- |

4. Esterases

| | |
|---|---|
| Various | Acetate-- |
| | Chloroacetate-- |
| | Butyrate- |

5. Inorganic esterases

| | |
|---|---|
| Phosphatase | HO(OO)PO-- |
| Sulphatase | HO(OO)SO— |

Part B: Chromogenic (coupler) components
(--all linking through hydroxyl or amine groups)

Hydroxybenzine (Phenol)
4-chloro-1-Hydroxybenzine (4-Chlorophenol)
2-chloro-1-hydroxybenzine (2(chlorophenol)
Aminobenzine (anilin)
4-chloro-1-aminobenzine (4-chloro-1-aminobenzine)
2-chloro-1-aminobenzine (2-chloro-1-aminobenzine)
1-Naphthol
2-Naphthol
4-chloro-1-naphthol
8-hydroxy-naphthaline-1-sulphonic acid
4-nitrophenol
2-chloro-4-nitro-phenol
2-chloro-4-nitro-1 naphthol
5-nitro-8-hydroxy-naphthalene-1 sulphonic acid Scavengers In the present context, a scavenger is a compound with the chemical coupling characteristics of the photographic color couplers, i.e., will react with a photographic developer, but with minimal or no color contribution to the solution in the wavelengths where the measurements are to be made. Scavengers are effective competitors to the color coupling reaction in the same solution, except in the region where both enzymes are in close proximity, where the concentration of the free color coupler is expected to be much higher. It is possible for a single chemical compound to act as a scavenger under some assay conditions and as a color coupler under different assay conditions. 8-hydroxy-naphthalene sulphonic acid is an example. If it is the color coupler, then the scavenger with which it is paired will have either no color at all or will absorb in the far red part of the spectrum.

Exemplary scavnger compounds include 8-hydroxy naphthalene sulphonic acid; o-acetoacetanisidide; acetoacetamide; ethyl acetoacetate; 1-(4-hydroxyphenyl)-1H-tetrazole-5-thiol; 3-(2,4,6-trichlorophenyl)-aminopyrazoline-5-one; Tyramine; 3-Hydroxytyramine; 4-aminoantipyrine; 4-hydroxyantipyrine; 4-(hydroxymethyl)-4-methyl-1-phenyl-3-pyrazolidinone; 1-phenyl-3-pyrazolidinone; with acetoacetamide; 3-(2,4,6-trichlorophenyl)-aminopyrazoline-5-one; and 3-Hydroxytyramine preferred.

Scavengers need not be completely color free after coupling, but should have a narrow spectrum of color that does not interfere when the color of measurement is carefully chosen. For example, a naphthol or phenol-containing substrate always gives a blue color on coupling and absorbs best in the 650 to 690 nM region of the spectrum. A scavenger that absorbs at 410 to 450 nm, but not above 600 nm, when coupled with the same developer, provides a good matched pair.

Useful scavengers include chemical analogs of white couplers used in the photographic arts, and include soluble triazole and tetrazole compounds. Other white couplers are listed in, for example U.S. Pat. No. 6,013,428, incorporated by reference herein, and these compounds, or analogs of them, may be useful as scavengers to prevent unwanted color formation. However the requirements of photographic white couplers are not exactly the same as requirements for the present solution assay. The preferred scavengers for solution assay according to the present invention are compounds that remain soluble after coupling with the developer. In contrast, a number of the white couplers listed in U.S. Pat. No. 6,013,428 are designed to prevent diffusion from one layer of film to another layer after coupling. They have large hydrocarbon side chains that have no other purpose than to make them less soluble in water. Scavengers of this sort generally are not used in the present invention. The best criteria for an effective scavenger in the present invention include water solubility before and after coupling, long term stability in aqueous solutions, no color before or after coupling in the spectral region of measurement, and no interaction with the enzymes used in the assay.

Analyte Molecule with Enzymatic Activity

In an alternative embodiment of the invention, the analyte molecule has the additional reactive property of one of the enzymes described above. In this embodiment, only one enzyme-conjugated ligand is required for the preferred reaction. When the enzyme bound ligand reagent attaches to the specific analyte it effectively forms an enzyme pair. One example of this is the detection of fetal hemoglobin with an antibody to fetal hemoglobin conjugated to alkaline phosphatase. Fetal hemoglobin acts as a pseudoperoxidase and the proximity of the hydrolytic enzyme to the analyte (having oxidase activity) satisfies the conditions herein described.

In one embodiment, a hydrolase, e.g., alkaline phosphatase, conjugated to a boronic acid moiety, e.g., aminophenyl boronic acid, is used as a ligand. This compound attaches to glycated hemoglobin as well as other glycated proteins. However only glycated hemoglobin has the pseudoperoxidase activity to provide the proximity of reaction products to satisfy the conditions of the present invention. One useful assay example is detection of glycated hemoglobin in the presence of other glycated proteins and of non glycated hemoglobin by use of boronate conjugate of alkaline phosphatase because only the glycated hemoglobin acts as ligand-pair for boronate and acts as an enzyme as well. Other boronic acid moieties, e.g., butyl boronic acid, can also be used.

In some embodiments, as described herein, the analyte may have a hydrolytic enzyme activity. Analytes with hydrolytic activity include components of the blood clotting cascade of enzymes, the enzymes involved in programmed cell death (caspases), and phosphatases that may be circulating in blood plasma normally or during a disease process.

Enzyme with Substrate Binding Activity

In a particular alternative embodiment of the invention, the analyte is an enzyme. Certain enzymes also strongly attach their substrates to their active sites. After operating on the substrate, the product is released. Inhibitor compounds similar to the substrate can be synthesized which attach even more strongly to the active site of the enzyme, and do not permit subsequent release. If such an enzyme is the analyte, then inhibitor with the characteristics described can be considered a ligand. Such a ligand may be conjugated directly or indirectly to an enzyme used as reagent in the present invention. One example of such a ligand, described by N. A. Thornberry and Y. Lazebnik, 1998, *Science*, 281: 1312 is: Biotin-X-Val-Ala-Asp(OMe)—$CH_2F$ (where X is a linking group). This compound is the biotinylated derivative of Caspase Inhibitor I. It may be used in the present invention together with, for example, Avidin conjugated alkaline phosphatase to link the hydrolase enzyme indirectly to the Caspase analyte. A complete caspase assay design also would contain an antibody to the specific caspase conjugated to horseradish peroxidase, and also supplying the substrates both the phosphatase and peroxidase, as previously described.

Exemplary Assay Format

The assay of the invention can be carried out in a variety of formats. The following description is for illustration and not for limitation. In one embodiment, a multi-well plate, such as a 96-well plate, is used. The two enzyme-ligand conjugates used for detection are mixed in approximately equal amounts and, typically, in amounts calculated to be approximately equal to, or in small excess of, the highest concentration of the analyte to be detected. While the 96 well plate is kept at a constant, cold temperature, the solution of enzyme-ligand mix is distributed in wells of the 96 well plate. In a series of at least 6 wells there is distributed a series of dilutions of the analyte of known concentration. Preferably another 6 wells are used as duplicate for the analyte dilutions of known concentration. In at least one, but preferably at least 3 wells no analyte is placed but instead the same buffer, used for the analyte dilutions, is used in the same volume of buffer. The unknown analyte is then distributed into yet other wells. Preferably the unknown analyte is used in duplicate wells for each sample. When all samples and blanks have been placed in the wells, incubation is continued for time to allow ligand binding to occur, e.g., typically at least 15 minutes and up to 12 hours, but preferably for 30 minutes, at the same cold temperature.

On completion of incubation, the developing solution is added. Buffer concentration of all components including the developing solution is in the range of 10 to 200 mM. Preferably the buffer concentration is in the range of 20 mM to 100 mM, and is most preferably 50 mM.

For alkaline phosphatase paired with horseradish peroxidase, the pH of buffer is in the range of about 7.4 to about 10.4. More preferably the pH is in the range of about 8.0 to about 9.3 and most preferably is about 8.3. Concentration of hydrogen peroxide is in the range of 0.01 to 0.1%. More preferably the range of hydrogen peroxide concentration is 0.02 to 0.09% and most preferably hydrogen peroxide is used as 0.03% of the final solution. Substrates are used in concentration range of 50 $\mu$M to 10 mM. More preferably the substrate concentrations are used as 100 $\mu$M to 5 mM and most preferably in concentration of 1.5 mM. Color development is measured with a plate reader.

When the substrate pairs are the preferred N'-ethyl-N'ethyl-(2-methylsulfonamidoethyl)-2-methyl-1,4-phenylenediamine, and phenyl phosphate the preferred wavelengths of measurement are 694 nm and 405 nm. When a white coupler with slight yellow color is used, e.g., acetoacetamide, the preferred wavelengths of measurement are 694 and 450 nm in the plate reader. Following measurement at the appropriate wavelength pair, the result of measurement of the unknown is compared to the result of measurement of the reference analyte and the concentration of the unknown is determined by standard curve fitting methods.

In the preferred embodiment of the invention sample is added to a pre-mixed solution of the two enzyme conjugated ligands in wells in a 96 well plate. Sample is permitted to incubate with enzyme conjugated ligands for approximately one half hour, before adding the developer solution. The aqueous developer solution in the preferred embodiment contains a photographic developer or analogous compound, a phosphate substituted phenol analog of a protected color coupler, a white coupler or analog of same which remains soluble during the reaction time, hydrogen peroxide and a buffer to control the acidity of the solution. Color develops steadily in the solution containing all these components plus the enzyme pair. The preferred time of reading the color in a conventional plate reader is at approximately 1 hour. But readings can be made as early as 15 minutes and as late as 4 hours depending on the specific application and reagents.

Kits

The reagents useful for practicing the methods of the present invention can be provided in kit form. In one embodiment, the kit comprises a container including separate vials of one or more of. (1) a hydrolase substrate that can be hydrolized to produce a color coupler (such as a specific color coupler listed herein); (2) an oxidizable developer (such as a specific oxidizable developer listed herein) (3) a hydrolase conjugated to antibody (4) an oxidase (such as a specific oxidase listed herein) conjugated to an antibody (5) a scavenger (such as a specific scavenger listed herein) (6) a buffer. Typically at least two or at least three of the above-listed reagents are included.

EXAMPLES

All examples presented here are model experiments with dilution series of an analyte. The subject analyte of the experiment was dissolved in an aqueous solution (in the same buffer used in the remainder of the assay). A specified volume of a specified concentration of the analyte was placed in a first well of a row of 12 wells on a 96 well plate. An equal volume of buffer was placed in all 12 wells of the same row. After the analyte and buffer in the first well were thoroughly mixed, one volume equivalent was removed and transferred to the next well, where it was again mixed thoroughly. This process of double dilution was continued for all except the last or $12^{th}$ well, which was left as a blank. The excess volume from well 11 was discarded, so that all wells have an equal volume, while the concentration of analyte in the row of 12 wells varies from a maximum in the first well (well number 1) to a zero level in the last well (well number 12).

Example 1

Dilution Series of Avidin (Analyte) with Biotin-conjugated Enzymes

Conditions of assay: Buffer: 50 mM Tris hydroxymethyl aminomethane, adjusted to pH 8.3 with HCl. The buffer also contains sodium chloride, potassium chloride and magnesium chloride (i.e., 200 mL of final solution contained 0.605 g of Tris hydroxymethyl aminomethane, 1.15 g NaCl, 0.15 g KCl and 0.1 g $MgCl_2$. All volumes placed in the wells are 100 μL.

Solutions of Avidin, biotinylated alkaline phosphatase (AP-B) and biotinylated horseradish peroxidase (HRP-B), all from Sigma Chemicals, St. Louis Mo., were prepared as 0.05 mg/mL stock. A further dilution of Avidin was with 1.5 mL of buffer and 75 μL of Avidin stock solution. The enzyme conjugates were diluted by adding 50 μL of HRP-B and 8.5 μL of AP-B stock solutions to 10 mL of buffer. These first dilutions of stock were kept in an ice bath or in the refrigerator until used and are not retained as dilutions from day to day.

Developer solution was made up as 12 mL of buffer containing 300 μL of 3% hydrogen peroxide, 300 μL of a 50 mM stock solution of N'-ethyl-N'ethyl-(2-methylsulfonamidoethyl)-2-methyl-1,4-phenylenediamine, 150 μL of 3-amino-1-(2,4,6-trichlorophenyl)-2-pyrazolin-5-one, as scavenger, and 300 μL of 1-naphthol phosphate. All reagent stock solutions were prepared as 50 mM stocks.

100 μL of dilute Avidin solution was added to the first well and serially diluted as described above. An exact replica of this serial dilution was performed in the next set of 12 wells. 100 μL of diluted enzyme mix was added immediately after completion of the serial dilution. The prepared plate in which all wells contained Avidin (at various concentrations) as well as HRP-B and AP-B at constant concentration, was kept on a cold surface for 30 minutes. Packaged and frozen blue ice covered by several layers of wet paper towel provides a convenient cold surface. After 30 minute incubation, 100 μL of a developer solution is added, and a measurement is taken at time of mixing. In the experimental stage, measurements are taken at 5 minute intervals to confirm the optimum design time. The measurements reported for this experiment are taken at 1 hour after adding developer. The wavelength of measurement is absorbance at 450 nm subtracted from absorbance at 694 nm (OD 694–450 nm). The wavelengths of light absorbance measurement were determined by taking preliminary light absorption spectra separately of solutions of the reaction product of oxidized developer with the color coupler and the reaction product of the oxidized developer with scavenger. A filter setting on the plate reader that incorporates maximum absorbance of the developer-coupler product and minimum absorbance of the developer-scavenger product was chosen as the main wavelength. A filter setting where both compounds give minimum readings is chosen as the wavelength to be subtracted from the main wavelength.

Figure 2:
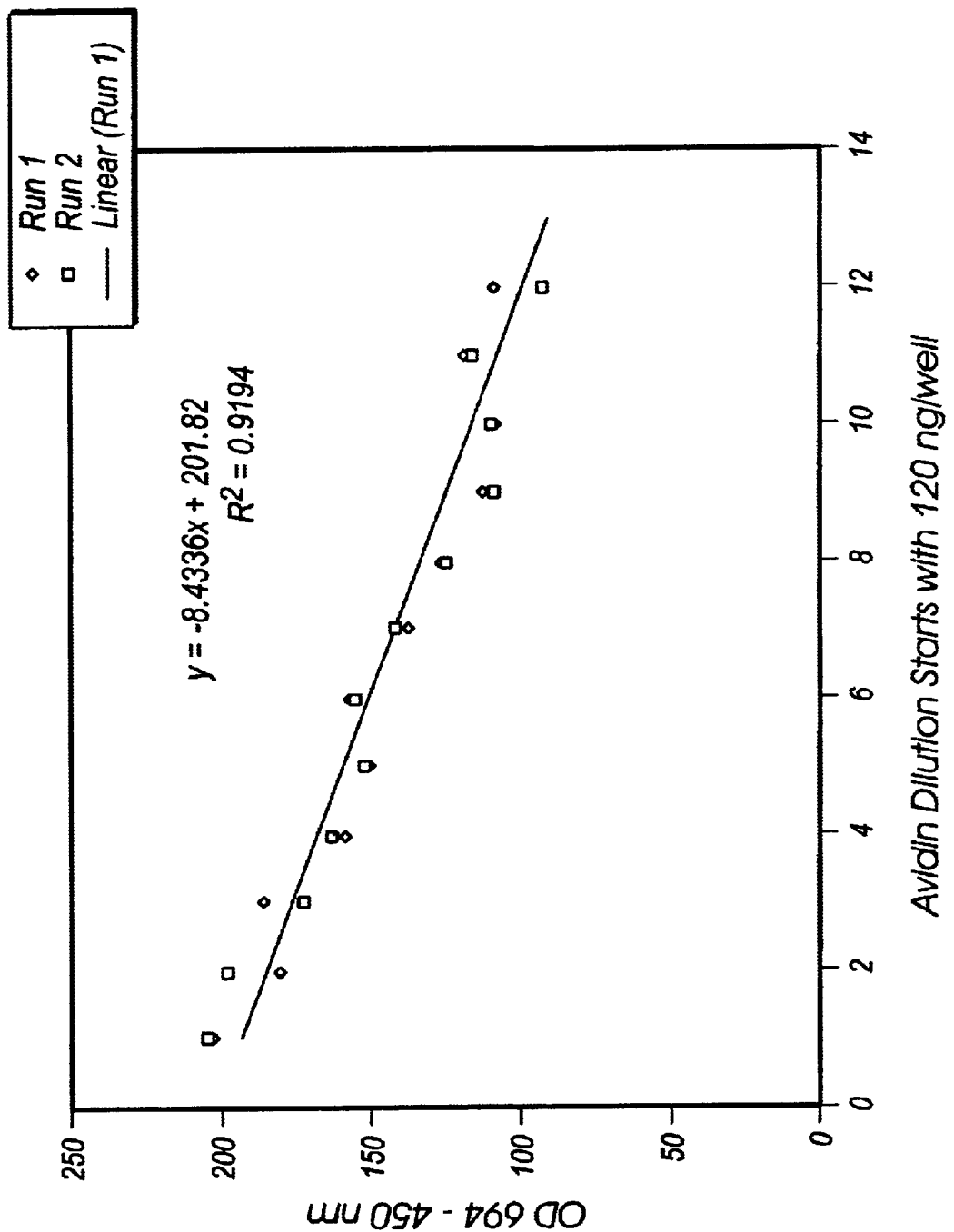
FIG. 2 provides results of a model solution assay, as described in Example 1.

Optical density measurements were transferred to a spreadsheet and the results are plotted. The results are presented in FIG. 2. It can be seen that the dilutions are in satisfactory linear order from the original 120 nanograms in the first well to the $9^{th}$ serial dilution. This is equivalent to slightly less than 0.5 nanograms or 500 picograms of Avidin. Since the molecular weight of Avidin is 60 kD the sensitivity of the measurement is in the order of 0.01 picomoles of the analyte.

In this experiment the proportion of AP-B to HRP-B is approximately 1:4 because 1-naphthyl phosphate produces 1-naphthol as color coupler. Under conditions of the assay 1-naphthol acts as a 4-equivalent coupler therefore more peroxidase than phosphatase activity is required.

If this experiment is repeated but alkaline phosphatase without biotin is substituted for AP-B, at the same activity as would be in the AP-B, all the wells read at approximately the background level of the above experiment. I.e. all readings are as if there is no Avidin in the solution, although the Avidin dilutions are as in the described experiment. Surprisingly, the methods of the present invention result in an efficient, quantitative colored third reaction product only when the first ligand and the second ligand are attached to the same analyte molecule.

Example 2

Phenyl Phosphate Substrate

Figure 3:
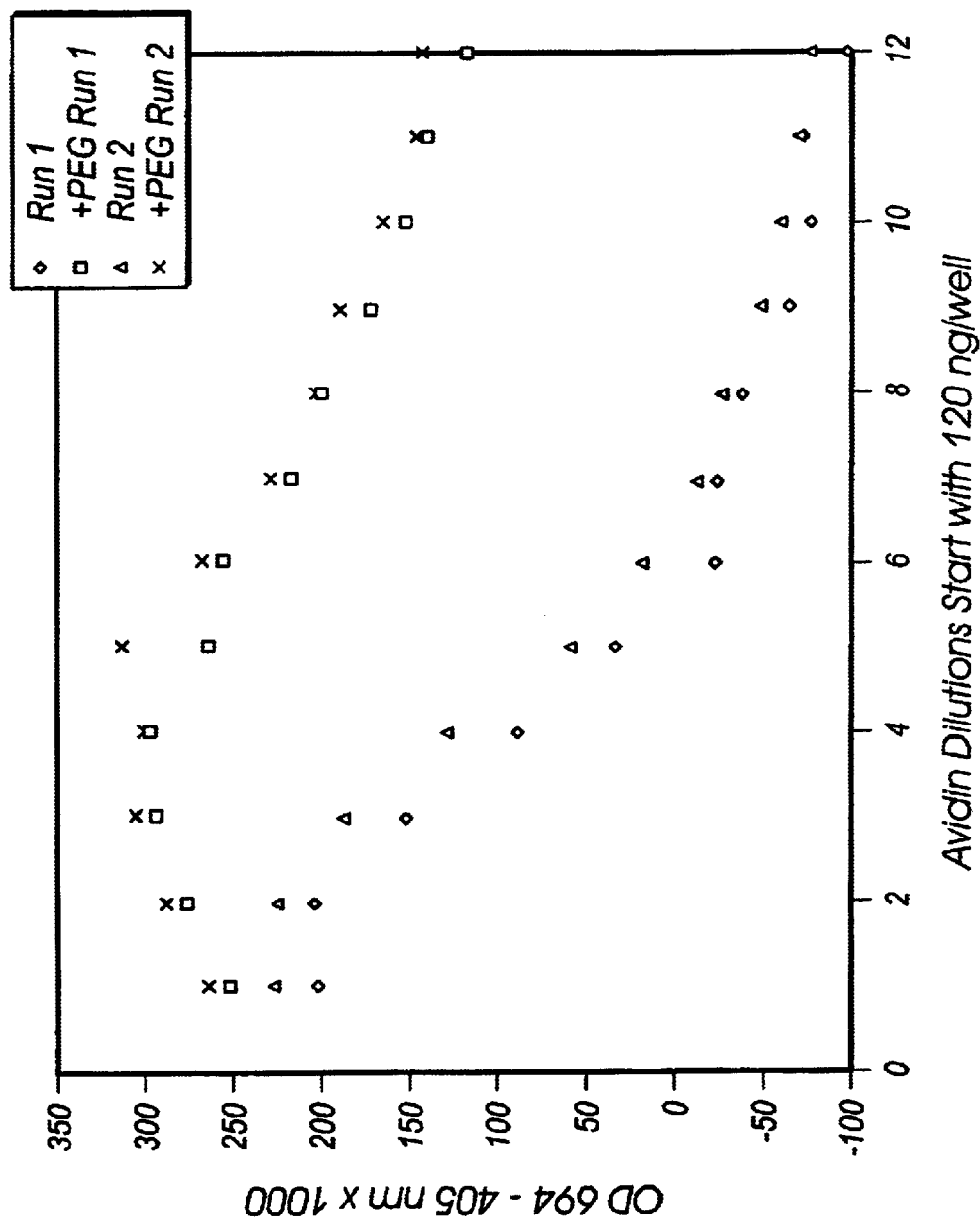
FIG. 3 provides results of a model solution assay, as described in Example 2.

This experiment has identical conditions to Example 1, except that AP-B and HRP-B were both used at 50 μL of stock in 10 mL of buffer, and the substrate for AP was phenyl phosphate. An additional set of wells is treated identically except that polyethylene glycol 600 was present in the developer at 4% concentration. The wavelengths of measurement were 694–405 nm, because the phenyl coupler has a different peak absorption and has no absorbance in the region of 400 nm. Results are presented in FIG. 3. The negative values are due to some absorbance of the 3-amino-1-(2,4,6-trichlorophenyl)-2-pyrazolin-5-one, acting as a scavenger, in the 405 nm region. In preliminary experiments it was found that four times the activity of alkaline phosphatase is required for phenyl phosphate than for naphthyl phosphate. Because AP acts less efficiently on phenyl phosphate than on 1-naphthyl phosphate, the proportions of enzyme were adjusted accordingly for this experiment. Avidin is a four valent molecule. That means that four biotinylated molecules can attach to one Avidin. As a result it is a good model analyte for determining the chemical interactions and for optimizing proportions of enzyme, and other reagents.

Results with polyethylene glycol 600 demonstrate that substances other than the main reactants may interfere with the reaction. In this case there is an enhancement of sensitivity, possible due to volume exclusion effects of PEG. Use of a standard curve accounts for such effects.

Example 3

Use of a Colorless Scavenger with Phenyl Phosphate Substrate

Figure 4:
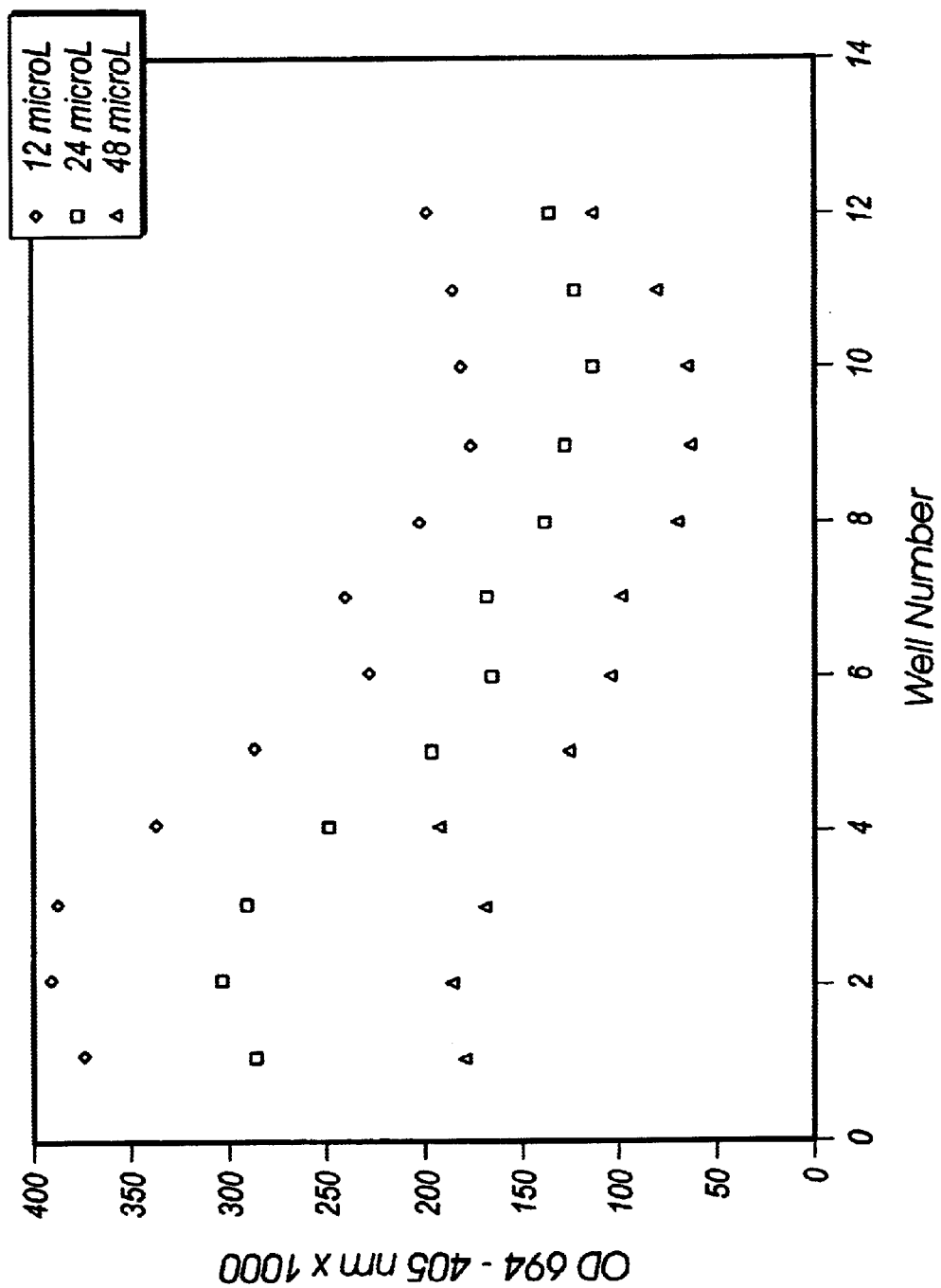
FIG. 4 provides results of a model solution assay, as described in Example 3.

The conditions of experiment 2 were again repeated, but with use of phenyl phosphate, and with equal amount volumes of stock HRP-B and AP-B. In addition, the scavenger used in experiments 1 and 2 was replaced with 12, 24 or 48 µL acetoacetamide in 2 mL of developer solution. Readings were taken at 650–405 nm. Results provide a regression curve similar to FIG. 3, except that there are no negative values in the regression because the scavenger forms a colorless coupled compound with oxidized developer. See FIG. 4. Note that excess scavenger can compete with the main color reaction. I.e., all else being equal, using twice as much scavenger will reduce the color to about half, because the scavenger is competing everywhere. The optimum concentration of scavenger can be adjusted to eliminate background color with "no sample blanks" and yet produces maximum color with sample present.

These model experiments are used to demonstrate that conditions may be varied in an experimental model in order to suite requirements of a specific assay. The experimental conditions are sufficiently versatile to provide for the needs of assays of biological analytes.

Example 4

Dilution Series of a Low Concentration Biological Analyte

Granulocyte Monocyte colony stimulating factor (GM-CSF), antibody to GM-CSF conjugated with HRP, and a second antibody against GM-CSF conjugated with AP were obtained from R & D Systems, Minneapolis MN. The GM-CSF and antibodies were prepared as stock solutions (0.05 mg/mL) in Tris buffer with sodium, potassium and magnesium chlorides adjusted to pH 7.4. 200 mL of the final buffer solution contains 0.605 g of Tris hydroxymethyl aminomethane, 1.15 g NaCl, 0.15 g KCl and 0.1 g $MgCl_2$.

A dilution series of GM-CSF was prepared as described supra, with the concentration ranging from 40 ng/100 µL in well number 1, and subsequent 1:1 dilutions in buffer in wells 2–11 (with well 12 left as a blank). Antibody is supplied to the final mix as 50 µL of each stock in 10 mL buffer. (All biologicals are made up as 0.05 mg/mL as stock. The dilution for this experiment was 50 µL in 10 mL, i.e., a 200 fold dilution from stock before adding 50 µL to each well. This is equivalent to 6.25 ng/well.)

Figure 5:
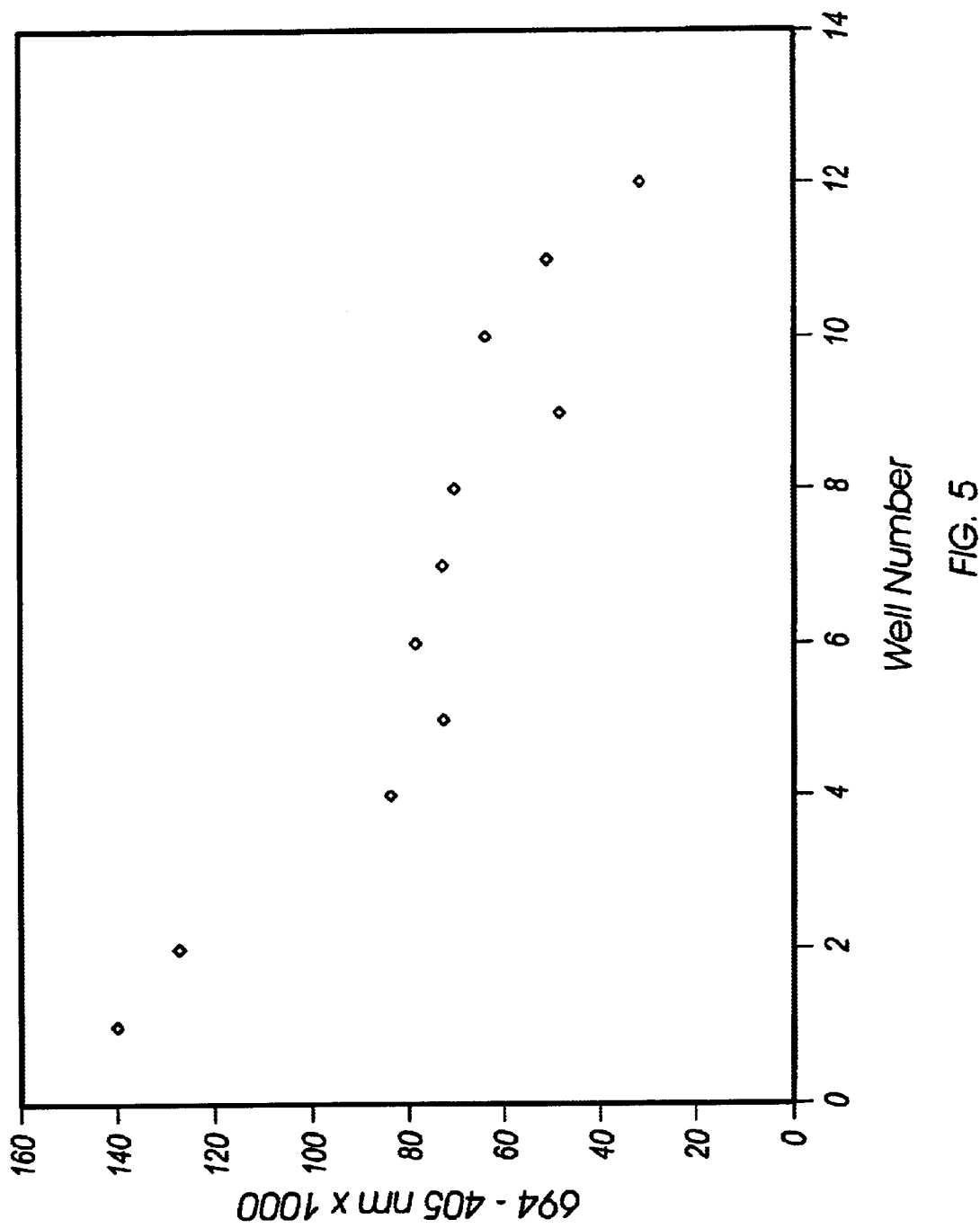
FIG. 5 provides results of an assay for GM-CSF, as described in Example 4.

The developer was as in experiment 3, with acetoacetamide as scavenger and phenyl phosphate as substrate, except that the pH of the developer was adjusted to 10. When the developer was added to each well the final pH is 8.3. Thus the ligand incubation was at pH 7.4 and the color development was at pH 8.3. The results shown in FIG. 5 were after incubation overnight. However, similar results were obtained with shorter, room temperature incubations (e.g., 1–2 hours). Color development was for one hour. The results again show a dose response regression when plotted graphically.

This experiment has sensitivity to approximately 0.04 nanograms which is equivalent to 0.025 picomoles because the molecular mass of GM-CSF is approximately 14,000 D.

Example 5

Determine Percent Glycated Hemoglobin in a Solution Assay

In this example the buffer used was different from Examples 1–4, because Tris buffer acts as competitor for the ligand, aminophenyl boronic acid. The analyte, glycated hemoglobin, and a control protein, non-glycated hemoglobin were prepared by column chromatography. The column was charged with aminophenyl boronic acid agarose purchased from Isolab. The column was washed with dilute hydrochloric acid and then equilibrated with 100 mM glycylglycine (GG) buffer at pH 9.0. Whole blood was hemolized with GG buffer containing Triton-X 100 (as the hemolizing agent). The lysate was layered on the column and left to stand for 5 minutes, during which time the glycated hemoglobin in the blood sample attaches to the boronated agarose. The first fraction, the non-glycated hemoglobin, was then eluted with GG buffer at pH 9.0. The peak of this fraction was isolated and preserved for further processing. The second fraction was then eluted with Tris buffer pH 8.6, containing 50 mM sorbitol. The peak of this fraction was also collected for further processing. The column was then renewed with dilute hydrochloric acid and was equilibrated again with GG buffer. The first fraction was again put over the same column, to ensure that there was no glycated hemoglobin remaining. Once eluted, this first fraction and the second fraction are individually dialyzed in a large volume of GG buffer and then re-concentrated with polyethylene glycol in GG buffer external to the dialysis bag. This procedure provided a solution of 0% glycohemoglobin (Hb) and a solution of 100% glycohemoglobin (GHb) in GG buffer.

Alkaline phosphatase conjugated with aminophenyl boronic acid (AP-Bor) was supplied by R & D Systems, Minneapolis, Minn. The stock solution of AP-Bor was made up as 0.05 mg/mL in GG buffer with magnesium chloride.

In the model assay, the GHb and Hb fractions are first made up to equal optical density solutions by diluting each by a factor of approximately 20 times, and further diluting the Hb fraction to adjust to the OD of the GHb fraction. These equal OD solutions were then mixed in proportions to provide GHb to total hemoglobin of 0, 5, 15, 33, 50, 66,7 and 100%. In a parallel experiment frozen pooled patient sample with Hb/GHb values established by the supplier (Primus Corporation, Kansas City, Mo.), were used in a similar way. These samples are with known GHb of 6.4, 7.5, 10, 12, 13.7, and 18.9%, which covers the clinical expected range.

When 50 µL of each analyte sample described in the previous paragraph was placed in individual wells of a 96 well plate, the optical density at 540–694 nm is approximately 0.15 OD. This first well content is then serially double diluted with buffer, and the useful dilutions are the first 4 or five as discovered by preliminary experiment. The optical density of all dilutions was recorded before further treatment. This 96 well plate was kept on a cold surface until the developer is added.

A solution of AP-Bor was further diluted from stock, by adding 25 µL of stock to 10 mL of GG buffer and mixing. This solution was maintained in an ice bath until used. 100 µL of dilute AP-Bor was added to each well of the 96 well plate. Incubation was for 40 minutes.

Developer solution was composed of 11 mL of GG buffer to which is added 1 mL of 50 mM acetoacetamide, 300 µL of 3% hydrogen peroxide, and 300 µL of each of 50 mM naphthyl phosphate and N'-ethyl-N'ethyl-(2-methylsulfonamidoethyl)-2-methyl-1,4-phenylenediamine. This was also made up fresh for each assay and kept cold until used. 100 µL was added to each well after the incubation is complete. The plate was transferred to a plate reader and optical density was monitored at 5 minute intervals for thirty minutes at 694–490 nm. Results of the assay with purified GHb and Hb are shown in Table 2. Results of the assay with frozen pooled human samples supplied by Primus Corporation are shown in Table 3. It can be seen that the assay satisfies the requirements for linearity, which provide evidence for both accuracy and reproducibility.

TABLE 2

OD 694–490 nm of GHb diluted with Hb
Developed as in example 5. Normalized to 0 GHb

| GHb Concentration | 4 µL | 3 µL | 2 µL | 1 µL | 0.5 µL | 0.25 µL |
|---|---|---|---|---|---|---|
| 0.00 | 0 | 0 | 0 | 0 | 0 | 0 |
| 33.33 | 281 | 174 | 80 | 57 | 44 | 35 |
| 50.00 | 392 | 252 | 132 | 100 | 62 | 56 |
| 66.67 | 494 | 341 | 172 | 109 | 73 | 63 |
| 100.00 | 691 | 486 | 257 | 164 | 116 | 89 |
| 15.00 | 127 | 68 | 25 | −8 | −7 | 12 |
| 5.00 | 45 | 36 | 65 | 64 | 66 | 64 |
| slope | 6.948185 | 0.700435 | 0.492132 | 0.664246 | 0.685773 | 0.717647 |
| intercept | 21.99859 | −9.26896 | 9.02533 | 0.06226 | 2.959212 | 9.278984 |
| r | 0.99657 | 0.997572 | 0.977143 | 0.971103 | 0.976559 | 0.978467 |

TABLE 3

Glycated hemoglobin % determined by solution assay using frozen pooled patient samples.

| Expected | Actual |
|---|---|
| 6.4 | 4.27905 |
| 7.5 | 7.319253 |
| 10 | 10.9135 |
| 12 | 11.18437 |
| 13.7 | 13.06465 |
| 18.9 | 19.1984 |
| Slope | 1.099554 |
| Intercept | −1.56004 |
| r | 0.982899 |

It is understood that the examples and embodiments described herein are for illustrative purposes only and that various modifications or changes in light thereof will be suggested to persons skilled in the art and are to be included within the spirit and purview of this application and scope of the appended claims. All publications, patents and patent applications cited herein are hereby incorporated by reference in their entirety for all purposes to the same extent as if each individual publication, patent or patent application were specifically and individually indicated to be so incorporated by reference.

I claim:

1. A method for detecting an analyte in solution comprising
   a) combining
   i) a solution to be assayed for the presence or amount of the analyte;
   ii) a first ligand that binds the analyte, wherein said first ligand is directly or indirectly bound to a hydrolase that cleaves a first substrate to produce a colorless first product;
   iii) a second ligand that binds the analyte, wherein the second ligand is directly or indirectly bound to an oxidase that oxidises a second substrate to produce a colorless second product;
   iv) said first substrate;
   v) said second substrate;
   vi) a compound that is a scavenger for the first product or the second product in step (a); and,
   whereby the hydrolase cleaves the first substrate to produce the first product and the oxidase oxidizes the second substrate to produce the second product,
   wherein the first product and the second product chemically combine, forming a covalent chemical linkage between the first product and second product, to produce a detectable reaction product, said detectable reaction product being a colored reaction product;
   b) detecting the production of the colored reaction product;
   c) relating the production of the colored reaction product with the presence or amount of analyte in the solution.

2. The method of claim 1 wherein the binding of the first ligand to the analyte does not interfere with the binding of the second ligand.

3. The method of claim 1 wherein the scavenger is 3-amino-1-(2,4,6-trichlorophenyl)-2-pyrazolin-5-one or acetoacetamide.

4. The method of claim 1 wherein the first substrate is a compound that comprises a benzene ring or naphthalene structure with one active hydroxyl group.

5. The method of claim 4 wherein the first substrate is 1-naphthol phosphate or phenyl phosphate.

6. The method of claim 1 wherein the second substrate is selected from the group consisting of N,N-dimethyl paraphenylene diamine; N,N-diethyl paraphenylene diamine; N-phenyl paraphenylene diamine; N'-ethyl-N'ethyl-(2-methylsulfonamidoethyl)-2-methyl-1,4-phenylene diamine; 4 amino antipyrene; and N,N-dimethylamino benzidine.

7. The method of claim 1 wherein the first ligand is a first antibody that specifically binds the analyte and second ligand is a second antibody that specifically binds the analyte.

8. The method of claim 1 wherein the hydrolase is selected from the group consisting of a phosphatase, an esterase, a galactosidase, a lipase, a glucuronidase, an amidase, a peptidase, and a sulphatase.

9. The method of claim 1 wherein the hydrolase is alkaline phosphatase and the oxidase is horseradish peroxidase.

10. The method of claim 9 wherein the first substrate is naphthyl phosphate or phenyl phosphate and the second substrate is N'-ethyl-N'ethyl-(2-methylsulfonamidoethyl)-2-methyl-1,4-phenylenediamine.

11. The method of claim 1 wherein at least one of the first and second ligand is an antibody or a lectin.

12. The method of claim 7 wherein the hydrolase is selected from the group consisting of a phosphatase, an esterase, a galactosidase, a lipase, a glucuronidase, an amidase, a peptidase, and a sulphatase.

13. The method of claim 12 wherein the hydrolase is a phosphatase and the oxidase is a peroxidase.

14. The method of claim 13 wherein the hydrolase is alkaline phosphatase and the oxidase is horseradish peroxidase.

15. The method of claim 12 wherein the first substrate is 1-naphthol phosphate or phenyl phosphate.

16. The method of claim 12 wherein the second substrate is selected from the group consisting of N,N-dimethyl paraphenylene diamine; N,N-diethyl paraphenylene diamine; N-phenyl paraphenylene diamine; N'-ethyl-N'ethyl-(2-methylsulfonamidoethyl)-2-methyl-1,4-phenylene diamine; 4 amino antipyrene; and N,N-dimethylamino benzidine.

17. The method of claim 12 wherein the first substrate is naphthyl phosphate or phenyl phosphate and the second substrate is N'-ethyl-N'ethyl-(2-methylsulfonamidoethyl)-2-methyl-1,4-phenylenediamine.

18. The method of claim 12 wherein the scavenger is 3-amino-1-(2,4,6-trichlorophenyl)-2-pyrazolin-5-one or acetoacetamide.

19. The method of claim 3 wherein the scavenger is 3-amino-1-(2,4,6-trichlorophenyl)-2-pyrazolin-5-one.

20. The method of claim 3 wherein the scavenger is acetoacetamide.

21. The method of claim 3 wherein:
   a) the hydrolase is alkaline phosphatase and the oxidase is horseradish peroxidase; and
   b) the first substrate is naphthyl phosphate or phenyl phosphate and the second substrate is N'-ethyl-N'ethyl-(2-methylsulfonamidoethyl)-2-methyl-1,4-phenylenediamine.

22. The method of claim 7 wherein:
   a) the hydrolase is alkaline phosphatase and the oxidase is horseradish peroxidase;
   b) the first substrate is naphthyl phosphate or phenyl phosphate and the second substrate is N'-ethyl-N'ethyl-(2-methylsulfonamidoethyl)-2-methyl-1,4-phenylenediamine;
   c) the scavenger is 3-amino-1-(2,4,6-trichlorophenyl)-2-pyrazolin-5-one or acetoacetamide.

* * * * *